United States Patent
Zhang et al.

(10) Patent No.: US 9,551,808 B2
(45) Date of Patent: Jan. 24, 2017

(54) CT APPARATUS WITHOUT GANTRY

(71) Applicants: Nuctech Company Limited, Beijing (CN); Tsinghua University, Beijing (CN)

(72) Inventors: Jinyu Zhang, Beijing (CN); Hu Tang, Beijing (CN); Zhanjun Duan, Beijing (CN); Li Zhang, Beijing (CN); Ziran Zhao, Beijing (CN)

(73) Assignee: NUTECH COMPANY LIMITED, Beijing (CN)

( * ) Notice: Subject to any disclaimer, the term of this patent is extended or adjusted under 35 U.S.C. 154(b) by 424 days.

(21) Appl. No.: 14/140,105

(22) Filed: Dec. 24, 2013

(65) Prior Publication Data

US 2014/0185744 A1    Jul. 3, 2014

(30) Foreign Application Priority Data

Dec. 27, 2012  (CN) .......................... 2012 1 0581712

(51) Int. Cl.
G01N 23/04  (2006.01)
G01V 5/00  (2006.01)
G01T 1/29  (2006.01)

(52) U.S. Cl.
CPC ............ G01V 5/005 (2013.01); G01N 23/046 (2013.01); G01T 1/2985 (2013.01); G01N 2223/419 (2013.01)

(58) Field of Classification Search
CPC  G01N 2223/419; G01N 23/046; G01V 5/005; A61B 6/032; A61B 6/4007; A61B 6/4014; A61B 6/4266
See application file for complete search history.

(56) References Cited

U.S. PATENT DOCUMENTS 6,018,562 A * 1/2000 Willson ............... G01N 23/087
378/57
6,236,709 B1 * 5/2001 Perry .................. G01N 23/046
378/57
(Continued)

FOREIGN PATENT DOCUMENTS

CN          1626039 A    6/2005
CN      101011250 A    8/2007
(Continued)

OTHER PUBLICATIONS

Zhang, J., et al., "Stationary scanning x-ray source based on carbon nanotube field emitters," Applied Physics Letters, vol. 86, 184104, 4 pgs. (2005).

*Primary Examiner* — Glen Kao
(74) *Attorney, Agent, or Firm* — Christensen Fonder P.A.

(57) ABSTRACT

A CT apparatus without a gantry. The CT apparatus includes a scanning passage; a stationary X-ray source arranged around the scanning passage and including a plurality of ray emission focal spots; and a plurality of stationary detector modules arranged around the scanning passage and disposed opposite the X-ray source. At least some of the plurality of detector modules may be arranged substantially in an L shape, a semicircular shape, a U shape, an arc shape, a parabolic shape, or a curve shape when viewed in a plane intersecting the scanning passage. The invention ensures that the stationary gantry type CT system has a small size, and a high data identification accuracy.

18 Claims, 1 Drawing Sheet

(56) References Cited

U.S. PATENT DOCUMENTS

| | | | |
|---|---|---|---|
| 7,072,436 B2 * | 7/2006 | Pelc | A61B 6/032 378/12 |
| 7,103,137 B2 | 9/2006 | Seppi et al. | |
| 7,280,631 B2 | 10/2007 | De Man et al. | |
| 7,819,580 B2 | 10/2010 | Song et al. | |
| 7,848,485 B2 | 12/2010 | Hu et al. | |
| 8,565,371 B2 | 10/2013 | Bredno | |
| 2005/0111610 A1 | 5/2005 | De Man et al. | |
| 2006/0008047 A1 * | 1/2006 | Zhou | A61B 6/032 378/10 |
| 2007/0183560 A1 | 8/2007 | Popescu et al. | |
| 2008/0069420 A1 * | 3/2008 | Zhang | A61B 6/00 382/132 |
| 2009/0285353 A1 | 11/2009 | Ellenbogen et al. | |
| 2011/0299653 A1 | 12/2011 | Mishra et al. | |
| 2012/0033784 A1 * | 2/2012 | Matsuda | A61B 6/00 378/19 |

FOREIGN PATENT DOCUMENTS

| | | |
|---|---|---|
| CN | 101441183 A | 5/2009 |
| CN | 101738406 A | 6/2010 |
| CN | 101849837 A | 10/2010 |
| CN | 101978257 A | 2/2011 |
| CN | 102445703 A | 5/2012 |
| CN | 203012155 U | 6/2013 |
| CN | 203084216 U | 7/2013 |
| DE | 10 2006 015 356 A1 | 8/2007 |
| JP | 11-500229 A | 1/1999 |
| JP | 2005-110722 A | 4/2005 |
| JP | 2005-534009 A | 11/2005 |
| JP | 2009-128363 A | 6/2009 |
| JP | 2011-503584 A | 1/2011 |
| WO | WO 97/18462 A1 | 5/1997 |
| WO | WO 01/22120 A1 | 3/2001 |
| WO | WO 2004/010127 A1 | 1/2004 |
| WO | WO 2006/081614 A1 | 8/2006 |
| WO | WO 2007/068933 A1 | 6/2007 |
| WO | WO 2007/149751 A2 | 12/2007 |
| WO | WO 2008/027706 A2 | 3/2008 |
| WO | WO 2009/050626 A1 | 4/2009 |
| WO | WO 2009/101543 A1 | 8/2009 |
| WO | WO 2010/030270 A1 | 3/2010 |
| WO | WO 2013/078344 A1 | 5/2013 |

* cited by examiner

CT APPARATUS WITHOUT GANTRY

PRIORITY CLAIM

The present application claims priority to Chinese Patent Application No. 201210581712.8 filed on Dec. 27, 2012, which said application is incorporated by reference in its entirety herein.

BACKGROUND OF THE INVENTION

1. Field of the Invention

The present invention relates to a CT apparatus without a gantry, and in particular to a CT apparatus, without a gantry, for safety inspection.

2. Description of the Related Art

Application of CT technology to a safety inspection system is increasingly developed due to the superexcellent performance of CT technology in identification of substance density. However, since CT technology requires that data are acquired at different angles for data reconstruction, conventional X-ray radioscopy data are acquired at different angles by a gantry system rotating at a speed for reconstruction. Since rotary components are used, the apparatus has a complicated structure, loud operational noise, a great volume, and a high operation and maintenance cost. In recent years, with the increasing development of X-ray source technology, and especially with the advent of multi-beam X-ray sources based on carbon nanotube technology, new concepts are provided for data reconstruction at different angles in CT technology.

Triggering timing of ray emission focal spots of a carbon nanotube X-ray source is controlled in a time sequence. If the number of the ray emission focal spots of the X-ray source is enough, layout of receiving surfaces of a detector are effective, and timing control for emission and receiving is reasonable, sufficient quantity of data required for CT data reconstruction can be required for reconstruction in the CT technology independent of the rotary gantry system. With the advent of gantry-less CT technology, the problem of complicated data transmission confronted by the conventional CT technology is solved, and operational cost is lowered, and reliability is improved. However, since rotary components of a CT apparatus are eliminated by the gantry-less CT technology, the CT technology has higher requirements for layout of the ray source and detector of the CT apparatus. How to lay out the ray source and detector reasonably also becomes one of the difficulties confronted by gantry-less CT apparatus manufacturers.

The early gantry-less CT technology is generally applied in the field of medical inspection, the scanned object under inspection is relatively simple, and it can be ensured that the object is positioned at a constant position in a scanning passage. Therefore, in the commonest layout, the detector is laid out in the shape of a straight line or a circular arc, and CT reconstruction data are acquired in different angle directions by relative movement of the ray emission focal spots of the multi-beam X-ray source relative to the receiving surface of the detector. In early gantry-less CT systems, the influence of the scanning passage on the layout of the X-ray source and detector, i.e., how to ensure that the scanning passage is large enough while an overall size of the gantry-less CT apparatus is small, is not synthetically considered whether in the straight line-shaped layout or a circular arc-shaped layout. Therefore, when the gantry-less CT apparatus is applied in the field of safety inspection, it has a large overall size and a low inspection rate so as to be far from meeting a floor space of the gantry-less CT apparatus required for quick inspection in the field of safety inspection. In the field of safety inspection, a size of the scanning passage, and a scanning speed are two important factors affecting inspection effect. Therefore, a CT apparatus for safety inspection has a scanning passage remarkably larger than a medical CT apparatus, and a CT apparatus for safety inspection has a speed remarkably faster than a medical CT system. Furthermore, most safety inspection apparatuses are located in public regions. Therefore, radiation shield requirements for the apparatus itself are high. These bring many rigorous requirements for the design of the safety inspection apparatus.

SUMMARY OF THE INVENTION

Accordingly, an object of the present invention is to provide a CT apparatus without a gantry, for example, which has a small volume so that its floor space can be reduced.

In accordance with an aspect of the present invention, there is provided a CT apparatus without a gantry, comprising: a scanning passage; a stationary X-ray source arranged around the scanning passage and comprising a plurality of ray emission focal spots; and a plurality of stationary detector modules arranged around the scanning passage and disposed opposite the X-ray source.

In accordance with an aspect of the present invention, at least some of the plurality of detector modules are arranged in a substantially L shape when viewed in a plane intersecting the scanning passage. The plane is substantially perpendicular to the scanning passage or the plane is inclined with respect to the scanning passage.

In accordance with an aspect of the present invention, at least some of the plurality of ray emission focal spots of the X-ray source is arranged in a substantially straight line or broken line shape when viewed in a plane intersecting the scanning passage. The plane is substantially perpendicular to the scanning passage or the plane is inclined with respect to the scanning passage.

In accordance with an aspect of the present invention, the ray emission focal spots arranged in the substantially straight line or broken line shape include the head end ray emission focal spot and the tail end ray emission focal spot, the detector modules arranged in the substantially L shape include the head end detector module and the tail end detector module, an angle is formed by lines respectively connecting a center of the passage to the head end ray emission focal spot and the tail end ray emission focal spot, another angle is formed by lines respectively connecting the center of the passage to the head end detector module and the tail end detector module, and a sum of the two angles is larger than 180 degrees. Thereby, it is ensured that a data acquisition system can acquire enough scan data.

In accordance with an aspect of the present invention, ray beams emitted from the plurality of ray emission focal spots of the X-ray source are perpendicular to the scanning passage or a direction in which an object under inspection is advanced along the scanning passage, or are inclined with respect to the scanning passage or the direction in which the object is advanced.

In accordance with an aspect of the present invention, ray beams emitted from the plurality of ray emission focal spots of the X-ray source, and ray receiving surfaces of the detector modules are located in a single plane.

In accordance with an aspect of the present invention, ray receiving surfaces of the detector modules abut against one another end to end such that rays emitted from the plurality of ray emission focal spots cannot pass between the ray receiving surfaces.

In accordance with an aspect of the present invention, two straight lines can be formed by connecting central points of ray receiving surfaces of the detector modules and intersect at a point when viewed in a plane intersecting the scanning passage. The plane is substantially perpendicular to the scanning passage or the plane is inclined with respect to the scanning passage.

In accordance with an aspect of the present invention, the plurality of ray emission focal spots of the X-ray source, and ray receiving surfaces of the plurality of detector modules are arranged in the same plane, and directions of ray beams emitted from the plurality of ray emission focal spots of the X-ray source are substantially perpendicular to the corresponding ray receiving surfaces of the detector modules. The plane is substantially perpendicular to the scanning passage or the plane is inclined with respect to the scanning passage.

In accordance with an aspect of the present invention, each detector module can receive a ray emitted from at least one of the plurality of ray emission focal spots of the X-ray source.

In accordance with an aspect of the present invention, among the plurality of ray emission focal spots of the X-ray source and the plurality of detector modules, the corresponding ray emission focal spots and detector modules are arranged in the same plane. The plane is substantially perpendicular to the scanning passage or the plane is inclined with respect to the scanning passage.

In accordance with an aspect of the present invention, the plurality of ray emission focal spots are arranged in at least one row in a direction in which the scanning passage extends.

In accordance with an aspect of the present invention, the CT apparatus further comprises: a front collimator disposed between the plurality of ray emission focal spots and the detector modules for adjusting energies of ray beams from the ray emission focal spots.

In accordance with an aspect of the present invention, the front collimator is a correction grid.

In accordance with an aspect of the present invention, a distance between the front collimator and the ray receiving surfaces of the detector modules is larger than a distance between the correction grid and the ray emission focal spots.

In accordance with an aspect of the present invention, a distance between the front collimator and the ray receiving surfaces of the detector modules is at least five times as large as a distance between the correction grid and the ray emission focal spots.

In accordance with an aspect of the present invention, the correction grid is shaped in a fitted curve.

In accordance with an aspect of the present invention, the X-ray source is a carbon nanotube X-ray source.

The present invention can adopt a carbon nanotube X-ray source. By laying out the X-ray source and the detector modules reasonably, the present invention overcomes the disadvantages of the complicated structure and bulky volume of the conventional gantry-less CT apparatus, thereby achieving miniaturization of the CT safety inspection apparatus, reducing its floor space, and improving availability of the gantry-less CT system in a safety inspection site.

The gantry-less CT system based on the carbon nanotube X-ray source according to the present invention can ensure, by controlling emission of the carbon nanotube X-ray source and optimizing layout of a detector arm, that enough data required by the gantry-less CT system are acquired under the conditions of a small width size of the CT apparatus, thereby reducing its floor space and cost.

DETAILED DESCRIPTION OF THE EMBODIMENTS

A further description of the invention will be made as below with reference to embodiments of the present invention taken in conjunction with the accompanying drawings.

Figure 1:
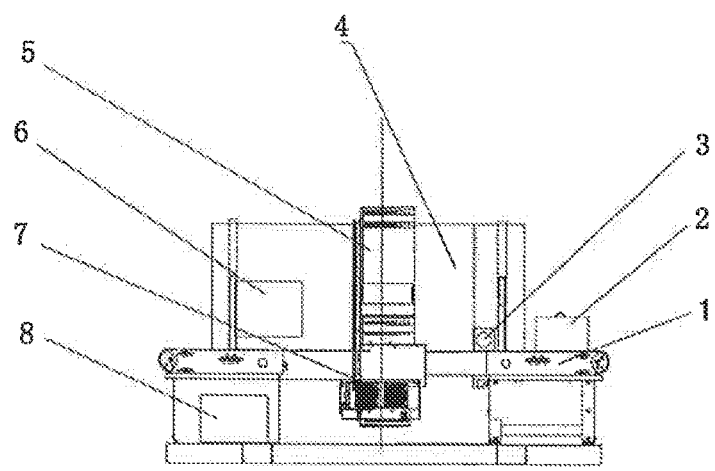
FIG. 1 is a schematic view of a CT apparatus without a gantry, according to an embodiment of the present invention.
Figure 2:
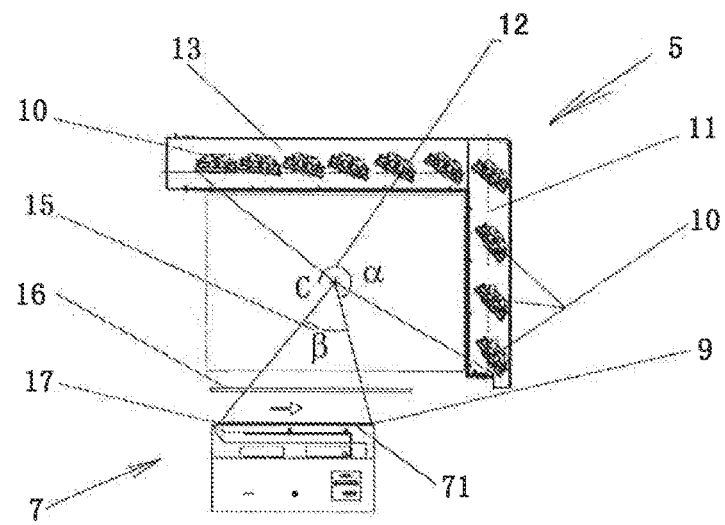
FIG. 2 is a schematic view showing layout of a ray source, a detector, and a front collimator, according to an embodiment of the present invention.
Figure 3:
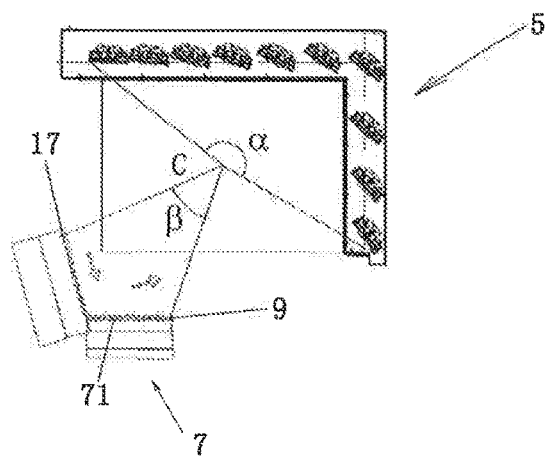
FIG. 3 is a schematic view showing layout of the ray source and the detector, according to an embodiment of the present invention.

As shown in FIGS. 1-3, a CT apparatus without a gantry according to an embodiment of the present invention comprises: a scanning passage 4; a stationary X-ray source 7 including a plurality of ray emission focal spots 71; and a plurality of stationary detector modules 10. The detector modules 10 are mounted on the detector arm 5, and the detector arm 5 is disposed opposite the X-ray source 7. Furthermore, the detector modules 10 are arranged in a substantially L shape when viewed in a plane intersecting the scanning passage 4 (the plane may be substantially perpendicular to the scanning passage or the plane may be inclined with respect to the scanning passage), i.e., there are a transverse arm 13 and a vertical arm 11 which are connected to each other without a gap therebetween. A plane in which the ray emission focal spots 71 of the X-ray source 7, and the detector arm 5 or the detector modules 10 are arranged is substantially perpendicular to the scanning passage 4 or a traveling direction of a transfer device 1, or is inclined with respect to the scanning passage 4 or the traveling direction of the transfer device 1. The plurality of ray emission focal spots 71 and the detector arm 5 or the detector modules 10 are arranged around the scanning passage 4. As illustrated in FIGS. 1-3, in an embodiment, the CT apparatus further comprises a photoelectric sensor system 3 for detecting entry and exit of an object under inspection into and from the scanning passage, an acquisition control unit 6, a computer reconstruction unit 8, and the transfer device 1 for transferring an object 2 under inspection.

The X-ray source 7 may be a carbon nanotube X-ray source with a plurality of X-ray emission focal spots 71. In addition, the X-ray source 7 may also be any other appropriate X-ray source so long as it includes a plurality of controllable ray emission focal spots. The plurality of ray emission focal spots of the X-ray source 7 are linearly arranged, and may be arranged in a straight line shape (as shown in FIG. 1) or a broken line shape (as shown in FIG. 3), a direction in which rays are emitted from the X-ray emission focal spots 71 is substantially perpendicular to the scanning passage 4 or the traveling direction of the transfer device 1, or is inclined with respect to the scanning passage 4 or the traveling direction of the transfer device 1, and the X-ray emission focal spots 71 and ray receiving surfaces of the detector modules 10 may be located in the same plane.

As shown in FIG. 2, all of the sectorial X-ray beams emitted by the X-ray source 7 can cover an effective scanning area 15 in the scanning passage 4 without being blocked and without uncovered region. Emission of the X-ray of each ray emission focal spot 71 of the X-ray source 7 is controlled by the acquisition control unit 6, and time when the X-ray emission focal spots 71 emit X-rays, intervals at which the X-ray emission focal spots 71 emit X-rays, and an intensity of the X-ray are adjustable. The ray emission focal spots 71 may be controlled to be triggered at intervals or continuously. An angle β is formed by lines respectively connecting a center C (of a cross section) of the passage 4 to the head end ray emission focal spot 9 and the tail end ray emission focal spot 17 of the X-ray source 7, another angle α is formed by lines respectively connecting the center C (of the cross section) of the passage to the head end detector module 10 and the tail end detector module 10 of the plurality of detector modules 10, and the two angles satisfy that a sum of β and α is larger than 180 degrees.

As shown in FIG. 2, the detector arm 5 comprises the transverse arm 13 and the vertical arm 11 which intersect without a gap therebetween. Central points of ray receiving surfaces of the detector modules 10 on the transverse arm 13 are located on a straight line, central points of ray receiving surfaces of the detector modules 10 on the vertical arm 11 are located on another straight line, and the two straight-line intersect at a point. The rays emitted from the plurality of ray emission focal spots 71 cannot pass through the detector arm 5. In a plane where the rays emitted from the X-ray emission focal spots 71 are located, the detector modules 10 abut against one another end to end without a gap therebetween. In other words, the rays emitted from all of the X-ray emission focal spots must meet the ray receiving surfaces of the detector modules. The detector module 10 shown in the figures may be composed of a linear array detector or a surface-array detector.

As shown in FIG. 2, the ray emission focal spots 71 are linearly arranged, and may be arranged in a straight line shape (as shown in FIG. 2) or a broken line shape (as shown in FIG. 3), when viewed in a plane intersecting the scanning passage 4. The sum of the angle β, formed by the lines respectively connecting the center C (of the cross section) of the passage to the head end ray emission focal spot 9 and the tail end ray emission focal spot 17 of the ray emission focal spots, and the angle α, formed by lines respectively connecting the center C of the passage to the head end detector module and the tail end detector module of the detector modules, is larger than 180 degrees, thereby ensuring that enough tomographic scan data can be acquired for reconstruction. In FIG. 3, a direction in which rays are emitted by the X-ray source is substantially perpendicular to the scanning passage 4 or a transfer direction of the transfer device 1, or is inclined with respect to the scanning passage 4 or the transfer direction of the transfer device 1, and the direction in which the rays are emitted corresponds to an orientation of the ray receiving planes of the detector modules.

Each detector module 10 on the detector arm 5 can receive rays emitted from at least some of the plurality of ray emission focal spots 71 of the X-ray source 7. Among the rays, some are perpendicular to the ray receiving surface, and some are inclined with respect to the ray receiving surface.

As shown in FIG. 2, the ray emission focal spots 71 are arranged in one row and the detector modules 10 are arranged in one row when viewed in the plane intersecting the scanning passage 4, and the direction in which the rays are emitted may be substantially perpendicular to the scanning passage 4 or the transfer direction of the transfer device 1, or is inclined with respect to the scanning passage 4 or the transfer direction of the transfer device 1. The ray receiving surfaces of the detector modules may be arranged in a single row or a plurality of rows in the traveling direction of the baggage transferring system. If the ray receiving surfaces are arranged in the plurality of rows, then a corresponding front collimator needs to be configured in a plurality of rows accordingly.

As shown in FIG. 2, the CT apparatus according to the present invention further comprises: the front collimator 16 disposed between the plurality of ray emission focal spots 71 and the plurality of detector modules 10 for controlling doses of the ray beams. The front collimator 16 may be a fitted curve-shaped correction grid or other appropriate correction grids. A distance between the front collimator 16 and the ray receiving surfaces of the detector modules 10 is at least five times as large as a distance between the front collimator 16 and the ray emission focal spots 71.

In the stationary CT apparatus without a gantry shown in FIG. 3, the detector arm 5 has an L-shaped structure, or the detector modules 10 are arranged in a substantially L shape, the ray emission focal spots 71 of the X-ray source 7 may also be arranged in the broken line shape. The sum of the angle β, formed by the lines respectively connecting the center C of the passage to the head end ray emission focal spot 9 and the tail end ray emission focal spot 17 of the ray emission focal spots 71, and the angle α, formed by lines respectively connecting the center C of the passage to the head end detector module 10 and the tail end detector module 10 of the detector modules 10, in an embodiment, is larger than 180 degrees. Alternatively, the detector modules 12 may also be arranged in any other shape such as a semicircular shape, a U shape, an arc shape, a parabolic shape, and a curve shape. The ray emission focal spots 71 of the X-ray source 7 may also be arranged in an L shape, a U shape, a semicircular shape, an arc shape, a parabolic shape, a curve shape, or the like.

In a period of time, X-ray energy reaching the detector modules 10 on the detector arm 5 may be emitted from a single ray emission focal spot 71 of the X-ray source 7, or from a combination of several ray emission focal spots 71 of the X-ray source 7. The intensities of the X-rays emitted from the different ray emission focal spots 71 of the X-ray source 7 may be program-controllable. A number of the ray emission focal spots of the X-ray source 7, and dimensions of the transverse arm and the vertical arm correlate with a size of the effective scanning area 15 within the scanning passage 4. The X-ray beams emitted from all of the ray emission focal spots 71 cover the scanning passage 4.

The triggering manner in which the X-ray emission focal spots 71 are triggered correlates with an acquisition control manner of the stationary CT apparatus, and whether the single X-ray emission focal spot 71 is triggered or not is controlled by the acquisition control unit 6 of the CT apparatus. The ray emission focal spots 7 of the X-ray source 7 may emit X-rays in sequence by instructions of the acquisition control unit 6, and the intervals and frequency at which the ray emission focal spots 7 emit the rays are controlled by the instructions of the acquisition control unit 6.

In the gantry-less system according to the present invention, the acquisition control unit 6 performs control, including control of the X-ray source 7 and control of the detector modules 10, through a Controller Area Network (CAN) bus. When a baggage 2 under inspection triggers the photoelectric sensor system 3, a computer system 8 transmits control instructions to the acquisition control unit 6 through a protocol to require the detector modules 10 to begin data acquisition. By parsing the instructions of the acquisition control unit 6, the acquisition control unit sends instructions for beginning data acquisition and transmits and error-corrects the acquired data, and the data acquired by the detector modules 10 are transmitted to the computer reconstruction unit 8.

The computer reconstruction unit 8 is a key device for achieving parsing and reconstruction of the data and characteristic identification in the gantry-less CT apparatus. When the acquired data are transmitted to the computer reconstruction unit 8, the computer reconstruction unit 8 firstly classifies the data according to the formats of the data packages, determines the sources of the data, and establishes a characteristic matrix based on the baggage scanned in the scanning area, and then solves the characteristic matrix to find a corresponding characteristic value. By comparing the characteristic value with a characteristic value of special substance in a data bank, the computer reconstruction unit 8 judges whether the substance in the baggage is a substance to which special attention should be paid and further provides a prompt about whether an alarm is raised.

The function of the scanning passage 4 is to provide a passage in which the scanned baggage 2 is transferred and travels, and a shield wall for shielding irrelevant X-rays. The shield wall is formed of a radiation protection material, and the radiation protection material may be a heavy metal such as lead or steal.

During inspection, the baggage 2 under inspection is transferred into the scanning passage 4 at a speed by the belt of the transfer device 1. When the baggage 2 triggers the photoelectric sensor system 3 or a photoelectric sensor 3, the X-ray source 7 is brought into a state ready for emission. When the baggage 2 enters the effective scanning area 15, the acquisition control unit 6 controls the ray emission focal spots 71 of the X-ray source 7 to emit electronic beams in a predetermined time sequence so as to generate X-rays continuously or at intervals. Meanwhile, the acquisition control unit 6 sends instructions for beginning data acquisition so that the detector modules 10 at the corresponding positions begin acquiring data. At the same time, time when the data are acquired and the positions of the detector modules 10 that acquire the data are recorded. The acquired data are transmitted to the computer reconstruction unit 8 through a dedicated cable such as an optical fiber. The computer reconstruction unit 8 corrects and processes the data by comparing instruction information for controlling the ray emission focal spot and acquired data information which occur within the same moment with each other, and then the data at the corresponding position of the baggage are reconstructed to establish a matrix based on substance characteristic of the scanned baggage 2. The matrix is conversely solved by a calculating module of the computer reconstruction unit 8 to obtain a single or a plurality of substance characteristics of the scanned baggage 2 at the corresponding position and establish the substance characteristic data within a single slice position. As the baggage 2 moves at a speed, the computer reconstruction unit 8 will acquire the substance characteristic data of the entire baggage slice by slice. By a dedicated identification algorithm, the data characteristics of the slices are collectively analyzed and determined and compared with a substance characteristic table in an existing data bank, to obtain a conclusion about whether or not the baggage 2 under inspection contains a special substance concerned by a user and display an image of the baggage by a display connected to the computer system.

In the present invention, data of the scanned baggage are acquired at different times by switching among the ray emission focal spots and among scanning and acquiring areas by switching among the ray emission focal spots 71 of the X-ray source 7 which are located at respective positions. As a result, a computerized tomography scan of the baggage under inspection can be achieved by the conventional computerized tomography (CT) technology without rotation of the scanned object or rotation of the detector and the X-ray source.

During reconstruction by the computer, an accuracy of the reconstruction of the tomography or slice data by the computer correlates with an angle at which the scanned baggage is observed. The present invention can adopt the X-ray source based on the carbon nanotube. Therefore, the ray emission focal spots may be arranged at the same intervals over a length. A sequence in which the ray emission focal spots emit rays may be arranged along a straight line or a broken line by program control performed by the acquisition control unit 6. The detector may comprise a linear array detector or a surface-array detector so as to solve the problem of the cost and identification accuracy of the system to the most degree.

Generally, the scanned baggage passes through the scanning area at a speed. In a case where high requirements for scanning are needed, the scanned object may remain stationary within the scanning area while it is being scanned, then moved by a displacement and after that the scanning of the object is continued while the object remains stationary until the scanning is completed. The computer system distinguishes substances by identifying the substance characteristics of the slices of the baggage. During identification of the substances, the system should identify at least one substance characteristic such as a density and an atomic number.

The gantry-less CT apparatus according to the present invention solves the problem that the conventional gantry-less CT apparatus has a bulky volume and a low acquisition accuracy, and achieves quick inspection and miniaturization of the CT safety inspection apparatus, by fully considering how the CT technology is applied to the field of safety inspection in such a way as to synthetically consider the scanning passage, the carbon nanotube X-ray source, and the detector system.

The invention claimed is:

1. A CT apparatus without a gantry, comprising:
a scanning passage;
a stationary X-ray source arranged around the scanning passage and comprising a plurality of ray emission focal spots; and
a plurality of stationary detector modules arranged around the scanning passage and disposed opposite the X-ray source, wherein
first detector modules of the plurality of detector modules are arranged in a first direction, second detector modules of the plurality of detector modules are arranged in a second direction, and the first detector modules and the second detector modules are disposed substantially in an L shape,
a first straight line can be formed by connecting central points of ray receiving surfaces of the first detector modules, a second straight line can be formed by connecting central points of ray receiving surfaces of the second detector modules and the first straight line and the second straight line intersect at a point when viewed in a plane intersecting the scanning passage, and
the ray receiving surfaces of the first detector modules are inclined relative to the first direction and substantially face the X-ray source, and the ray receiving surfaces of the second detector modules are inclined relative to the second direction and substantially face the X-ray source.

2. The CT apparatus of claim 1, wherein
at least some of the plurality of ray emission focal spots of the X-ray source are arranged in a substantially straight line or broken line shape when viewed in a plane intersecting the scanning passage.

3. The CT apparatus of claim 2, wherein
the ray emission focal spots arranged in the substantially straight line or broken line shape include a head end ray emission focal spot and a tail end ray emission focal spot, the detector modules arranged in the substantially L shape include a head end detector module and a tail end detector module, an angle is formed by lines respectively connecting a center of the passage to the head end ray emission focal spot and the tail end ray emission focal spot, another angle is formed by lines respectively connecting the center of the passage to the head end detector module and the tail end detector module, and a sum of the two angles is larger than 180 degrees.

4. The CT apparatus of claim 1, wherein
ray beams emitted from the plurality of ray emission focal spots of the X-ray source are perpendicular to the scanning passage or a direction in which an object under inspection is advanced along the scanning passage, or are inclined with respect to the scanning passage or the direction in which the object is advanced.

5. The CT apparatus of claim 1, wherein
ray beams emitted from the plurality of ray emission focal spots of the X-ray source, and the ray receiving surfaces of the detector modules are located in a single plane.

6. The CT apparatus of claim 1, wherein
the ray receiving surfaces of the detector modules abut against one another end to end such that rays emitted from the plurality of ray emission focal spots cannot pass between the ray receiving surfaces.

7. The CT apparatus of claim 1, wherein
the plurality of ray emission focal spots of the X-ray source, and the ray receiving surfaces of the plurality of detector modules are arranged in the same plane, and directions of ray beams emitted from the plurality of ray emission focal spots of the X-ray source are substantially perpendicular to the corresponding ray receiving surfaces of the detector modules.

8. The CT apparatus of claim 1, wherein
each detector module can receive a ray emitted from at least one of the plurality of ray emission focal spots of the X-ray source.

9. The CT apparatus of claim 1, wherein
among the plurality of ray emission focal spots of the X-ray source and the plurality of detector modules, the corresponding ray emission focal spots and detector modules are arranged in the same plane.

10. The CT apparatus of claim 1, wherein
the plurality of ray emission focal spots are arranged in at least one row in a direction in which the scanning passage extends.

11. The CT apparatus of claim 1, further comprising a front collimator disposed between the plurality of ray emission focal spots and the detector modules for adjusting energies of ray beams from the ray emission focal spots.

12. The CT apparatus of claim 11, wherein the front collimator is a correction grid.

13. The CT apparatus of claim 12, wherein
a distance between the front collimator and the ray receiving surfaces of the detector modules is larger than a distance between the correction grid and the ray emission focal spots.

14. The CT apparatus of claim 12, wherein
a distance between the front collimator and the ray receiving surfaces of the detector modules is at least five times as large as a distance between the correction grid and the ray emission focal spots.

15. The CT apparatus of claim 12, wherein
the correction grid is shaped in a fitted curve.

16. The CT apparatus of claim 1, wherein
the X-ray source is a carbon nanotube X-ray source.

17. The CT apparatus of claim 1, wherein
the plurality of ray emission focal spots of the X-ray source emit X-rays in sequence at intervals or continuously.

18. The CT apparatus of claim 1, wherein
the ray emission focal spots of the X-ray source are arranged in an L shape, a U shape, a semicircular shape, an arc shape, a parabolic shape, or a curve shape.

* * * * *